(12) United States Patent
Dumesnil

(10) Patent No.: US 10,426,563 B2
(45) Date of Patent: Oct. 1, 2019

(54) LIFESTYLE WEATHERPROOF WEARABLE BAG FOR VENTRICULAR ASSIST DEVICE

(71) Applicant: Custom Design and Development, Inc., Katy, TX (US)

(72) Inventor: Curtis Dumesnil, Katy, TX (US)

(73) Assignee: CUSTOM DESIGN AND DEVELOPMENT, INC., Katy, TX (US)

( * ) Notice: Subject to any disclaimer, the term of this patent is extended or adjusted under 35 U.S.C. 154(b) by 0 days.

(21) Appl. No.: 15/498,050

(22) Filed: Apr. 26, 2017

(65) Prior Publication Data

US 2017/0304017 A1    Oct. 26, 2017

Related U.S. Application Data

(60) Provisional application No. 62/327,573, filed on Apr. 26, 2016, provisional application No. 62/327,594, filed on Apr. 26, 2016.

(51) Int. Cl.

| | |
|---|---|
| *A45F 3/02* | (2006.01) |
| *A61B 50/31* | (2016.01) |
| *A45F 5/02* | (2006.01) |
| *A45F 3/12* | (2006.01) |
| *A61M 1/12* | (2006.01) |
| *A45F 3/00* | (2006.01) |

(52) U.S. Cl.
CPC .............. *A61B 50/31* (2016.02); *A45F 3/02* (2013.01); *A45F 3/12* (2013.01); *A45F 5/021* (2013.01); *A61M 1/122* (2014.02); *A45F 2003/001* (2013.01); *A61M 2205/8206* (2013.01); *A61M 2209/088* (2013.01)

(58) Field of Classification Search
CPC .......... A61B 50/31; A61M 1/122; A45F 3/02; A45F 3/01
See application file for complete search history.

(56) References Cited

U.S. PATENT DOCUMENTS

| | | | | |
|---|---|---|---|---|
| 44,993 | A * | 11/1864 | Woods ...................... | A45F 3/04 224/583 |
| 4,746,043 | A * | 5/1988 | Booker ..................... | A45F 5/00 150/154 |
| 5,059,182 | A * | 10/1991 | Laing .................. | A61M 5/1483 222/95 |

(Continued)

*Primary Examiner* — Derek J Battisti
(74) *Attorney, Agent, or Firm* — Bracewell LLP; Brad Y. Chin

(57) ABSTRACT

Embodiments provide a water-resistant VAD lifestyle bag including a removable strap connected to two connectors along the top of the bag, a lower unit having two curved top edges connected to two connectors and having at least one water bottle pocket to contain water bottles and a front pocket cover flap, a zipper configured along the top of the lower unit, an emergency information window made of clear material to view the status of a VAD device, a plurality of pockets built into the back of the bag, at least one credit card pocket built into the bag, a VAD controller pocket having clips and configured to secure a VAD controller, and at least one VAD battery pocket having clips and fitted to house at least one VAD battery for powering the VAD device. The plurality of pockets is configured to secure pens, phones, and snacks.

17 Claims, 6 Drawing Sheets

(56) References Cited

U.S. PATENT DOCUMENTS

| | | | | |
|---|---|---|---|---|
| 5,095,718 | A * | 3/1992 | Ormond | A45F 3/04 |
| | | | | 206/427 |
| 6,915,934 | B2 * | 7/2005 | Hassett | A45F 5/00 |
| | | | | 206/726 |
| 8,807,412 | B2 * | 8/2014 | Thomas | A45C 11/00 |
| | | | | 224/269 |
| 8,845,608 | B2 * | 9/2014 | Krasikoff | A61M 27/00 |
| | | | | 604/345 |
| 2006/0131206 | A1 * | 6/2006 | Kenney | A61B 50/31 |
| | | | | 206/570 |
| 2006/0276768 | A1 * | 12/2006 | Miller | A61J 1/165 |
| | | | | 604/403 |
| 2008/0011794 | A1 * | 1/2008 | Daniel | A45F 5/02 |
| | | | | 224/183 |
| 2010/0181220 | A1 * | 7/2010 | Dasara | A61B 50/31 |
| | | | | 206/438 |
| 2013/0310802 | A1 * | 11/2013 | Weinmann | A61J 1/10 |
| | | | | 604/506 |
| 2015/0265352 | A1 * | 9/2015 | Johnson | A61B 50/31 |
| | | | | 604/516 |

* cited by examiner

LIFESTYLE WEATHERPROOF WEARABLE BAG FOR VENTRICULAR ASSIST DEVICE

CROSS-REFERENCE TO RELATED APPLICATIONS

This application is a non-provisional patent application claiming priority to and the benefit of U.S. Prov. Pat. Apps. Ser. No. 62/327,573 and Ser. No. 62/327,594, each filed Apr. 26, 2016, the entire disclosures of which are expressly incorporated herein by reference.

BACKGROUND

Field

Embodiments generally relate to a water-resistant bag for storing a medical electronic device. More specifically, the invention relate to a water-resistant ventricular assist device (VAD) bag for carrying VAD devices, such as HeartWare® or HeartMate® devices, including, for example, Heart-Ware® or HeartMate® controllers and batteries, in showers or inclement weather conditions.

Description of the Related Art

Cardiac arrest and other cardiac health ailments are a major cause of death worldwide. Heart failure happens when the heart does not pump enough blood to meet the needs of a human body, causing fluid to build up in the lungs and body. Sometimes the heart becomes so weak that medicine cannot improve the symptoms. Often the only treatment option is a VAD.

VADs are mechanical pumps implanted into a human chest. VADs take over the pumping action of the area of the heart called the ventricle. VADs help a heart pump so that a person becomes stronger. A VAD system utilizes a centrifugal blood pump that is implanted into pericardial space for ventricular support. A percutaneous driveline connects the VAD mechanical pump to an external controller, which regulates the pump function and is powered by one or more batteries.

The use of VADs provides patient benefits in most conditions. The presence of water or moisture in contact with VADs is undesirable for many reasons. Water or moisture destroys electrical function of the VAD pumps and of the battery in a VAD system. Further, water or moisture partially or completely clogs components of the controller and is abrasive to components within the VAD pump. In addition, the constant or daily presence of water leaves rust on VAD system components, resulting in gradual wear and tear.

The restricted use of VADs in water environments or moisture conditions limits their benefits. VADs are not suitable for use in showers or in inclement weather. Plastic bags that cover VADs during showers or inclement weather are flimsy or do not provide adequate protection. Multiple plastic bags are oftentimes used to cover multiple components of the VAD system. Such plastic bags do not adequately seal compartments and components of the VAD system and do not properly position other lifestyle items. Further, plastic bag do not protect VAD devices from water and other debris that may stop the device from working while the wearer is in inclement weather.

Various kinds of backpacks or shoulder bags are available to protect a wearable component from water during various activities outside. These backpacks or shoulder bags are not designed for use with VAD devices and do not improve patient comfort and mobility while outside using the VAD device. Generally, bags are not custom designed for VADs and do not provide enough protection for the VAD, its controller, or batteries, while a patient is showering. Backpacks and shoulder bags can hold VAD devices, but are limited in restricting patient comfort and mobility while in the shower and using a VAD device. Such bags do not allow the user to quickly access the controls of a VAD system and replace the batteries. Such backpacks and shoulder bags are often bulky and do not have enough pockets to accommodate various VAD system components.

It is thus desirable to have a VAD bag that can quickly and easily be accessed and also one that provides water, moisture, and debris protection for the electronics contained in the bag itself while the user is in the shower or experiencing inclement weather. Further, it is desirable to have a VAD bag that allows the user to quickly access the controls and replace the batteries, and also one that provides protection for the electronics contained in the bag itself while the user is experiencing inclement weather. Accordingly, what is needed is a water-resistant bag for storing and protecting VAD devices, its controller, and batteries.

SUMMARY

Embodiments relates to a water-resistant VAD lifestyle bag, a water-resistant VAD lifestyle system, and a method of making a water-resistant VAD lifestyle bag for storing a VAD sensitive to water damage. More specifically, embodiments relates to a water-resistant VAD lifestyle bag including a removable strap connected to two connectors along the top of the bag and having a shoulder pad, a lower unit having two curved top edges connected to two connectors and having at least one water bottle pocket to contain water bottles of various shapes and a front pocket cover flap, a zipper configured along the top of the lower unit, an emergency information window made of clear material to view the status of a VAD device, a plurality of pockets built into the back of the bag, at least one credit card pocket built into the bag, a VAD controller pocket having clips and configured to secure a VAD controller, and at least one VAD battery pocket having clips and fitted to house at least one VAD battery for powering the VAD device. The plurality of pockets is configured to secure at least one of pens, phones, and snacks. The VAD controller pocket is configured to block entry of moisture to the VAD controller. The VAD battery pocket is configured to block entry of moisture to the at least one VAD battery. The VAD controller pocket and the at least one VAD battery pocket is outlined with polypropylene piping with a ⅛ inch polypropylene cord, lined with waterproof lining of 200 Denier Oxford Coated DWR fabric, and contains a styrene insert to maintain the firm shape of the bag. The at least one water bottle pocket is constructed of 1,000 Denier Nylon Cordura Coated DWR $1^{st}$ Fabric and having a plastic inserted of 0.25 inch thick plastic. The emergency information window is constructed of 30,000 super clear plastic and with a zipper chain of 8 inches length. The plurality of pockets is constructed of 1,000 Denier Oxford Coated DWR $1^{st}$ fabric and optionally sewn over with water-resistant lining fabric.

Another embodiment provides a water-resistant VAD lifestyle bag that is 12 inches long at the top of the bag, 13.5 inches high, 11 inches long at the bottom of the bag or is 14.25 inches long at the top of the bag, 11.5 inches high, and 11.5 inches long at the bottom of the bag, and with a 2 inches seam ending at the top of the bag. In some embodiments, the water-resistant VAD lifestyle bag provides at least one belt loop sewn onto the back of the bag for holding onto a belt and with seams 2.25 inches apart and made of P 2,200 with 2,000 webbing with UV inhibitors or a sewn extra pocket 4.75 inches by 2.25 inches coupled with a zipper onto the back of the bag. The emergency information window is 6.5 inches by 6.5 inches. The VAD battery pocket is 4.25 inches by 3.25 inches by 1.75 inches. The plurality of pockets further includes at least one of a pen pocket 0.25 inch by 6 inches, a phone pocket of 5.25 inches by 7.25 inches, and a snack pocket 7 inches by 4 inches. The at least one water bottle pocket includes a bottom hole of ⅝ inch and is 6 inches tall by 7 inches around. The at least one credit card pocket includes a first credit card pocket 5 inches by 2.25 inches, a second credit card pocket 4.75 inches by 2.25 inches, a third credit card pocket 4.25 inches by 2.25 inches, a fourth credit card pocket 4⅜ inches by 2.25 inches, and a fifth credit card pocket 4.25 inches by 2.25 inches. The removable strap is 56 inches in length. The zipper is a #8 zipper chain of 10 inches long or a #10 zipper chain of 12 inches long, with water-resistant lining fabric. The bag exterior of the bag is constructed of a double layer, water-resistant lining fabric with a foam inserted between the lining fabric layers to create firmness and maintain shape, wherein the foam is ⅛ inch polypropylene, dust-free, non-abrasive, shock resistant and moisture proof sewn with German Thread Strongbond 40-T70 V69 and Serabond 30-T90-V92 with up to 12 stiches per inch.

According to at least one embodiment, the water-resistant VAD system includes a water-resistant VAD lifestyle bag and a water-resistant percutaneous lead for electrically coupling the VAD controller to a VAD pump and for regulating VAD pump function. In some embodiments, the water-resistant VAD system further includes an external display device for presenting performance of the water-resistant VAD lifestyle system or for providing touch input to the controller operating parameters.

According to at least one embodiment, the method of making a water-resistant VAD lifestyle bag for storing a VAD device sensitive to water damage including providing a removable strap connected to two connectors along the top of the bag and having a shoulder pad, providing a lower unit having two curved top edges connected to two connectors and having at least one water bottle pocket to contain water bottles of various shapes and a pocket cover flap, closing the VAD controller pocket with the clips, and closing the VAD battery pocket with the clips.

BRIEF DESCRIPTION OF DRAWINGS

These and other features, aspects, and advantages of the invention are better understood with regard to the following Detailed Description, Claims, and accompanying Figures. It is to be noted, however, that the Figures illustrate only various embodiments of the disclosure and are therefore not to be considered limiting of the invention's scope as it can admit to other equally effective embodiments.

DETAILED DESCRIPTION

Figure 1:
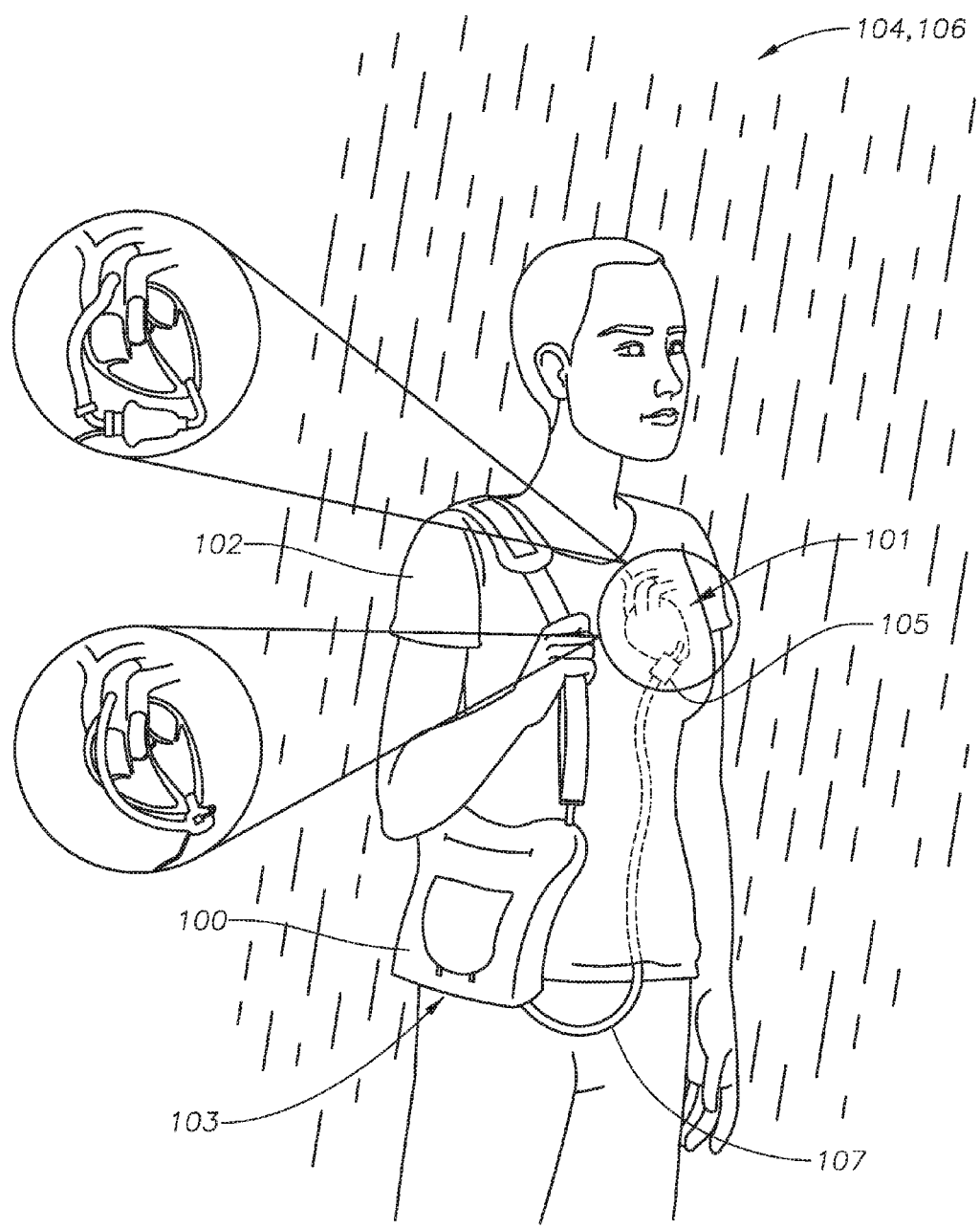
FIG. 1 is a full view of the water-resistant VAD lifestyle bag for use in a shower or in inclement weather.

The foregoing aspects, features, and advantages of the various embodiments will be further appreciated when considered with reference to the following description of preferred embodiments and accompanying drawings, wherein like reference numerals represent like elements. The following is directed to various exemplary embodiments of the disclosure. The embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment. Like numbers refer to like elements throughout. In an embodiment, usage of the term "about" includes +/−5% of the cited magnitude. In an embodiment, usage of the term "substantially" includes +/−5% of the cited magnitude.

For simplicity and clarity of illustration, the drawing figures illustrate the general manner of construction, and descriptions and details of well-known features and techniques may be omitted to avoid unnecessarily obscuring the discussion of the described embodiments of the invention. Additionally, elements in the drawing figures are not necessarily drawn to scale. For example, the dimensions of some of the elements in the figures may be exaggerated relative to other elements to help improve understanding of the various embodiments. Like reference numerals refer to like elements throughout the specification. Hereinafter, various embodiments will be described in detail with reference to the accompanying drawings.

FIG. 1 is a full view of the water-resistant VAD lifestyle bag 100 for use in a shower 104 or in inclement weather 106 by a patient 102. A water-resistant VAD lifestyle system 103, which may include a VAD pump 105, a water-resistant percutaneous lead 107, a water-resistant VAD lifestyle bag 100, a VAD controller 138 (shown in FIG. 3A), and one or more VAD batteries 144 (shown in FIG. 3A and FIG. 3C), may be used to maintain blood to the patient 102 while in a wet environment. Thus, for example, the function of the water-resistant VAD lifestyle system 103 is maintained while the patient 102 partakes in daily activities that may involve exposure to water, moisture, or debris in the external environment. In some embodiments, the water-resistant percutaneous lead 107 and water-resistant VAD bag 100 protect internal electrical components from the water in any wet environment. In certain embodiments, the water-resistant VAD lifestyle system may include an external display device for presenting performance of the water-resistant VAD lifestyle system 103 or for providing touch input to the controller operating parameters by a patient 102.

As shown, the water-resistant percutaneous lead 107, which electrically couples the VAD controller (shown in FIG. 3A) to the VAD pump 105 and which regulates the VAD pump 105 function, may be waterproof or covered with a water-resistant material. The VAD pump 105, which may be a centrifugal blood pump that is implanted into pericardial space for ventricular support, is located inside of the patient 102 and is not exposed to water. In some embodiments, for example, the water-resistant VAD lifestyle bag 100, when coupled together with the water-resistant percutaneous lead 107 and the VAD pump 105 provides water resistance to the entire water-resistant VAD lifestyle system 103 for use in a shower 104 or in inclement weather 106. Thus, for example, a patient 102 can comfortably shower or remain mobile while still utilizing the exemplary water-resistant VAD lifestyle system 103 of the various embodiments.

As shown in the close-up of the heart region 101, the VAD pump 105 may be a HeartMate® II Blood Pump or a Heartware® Blood Pump. In certain embodiments, a pacemaker or a Heartware® monitor may take the place of the VAD pump 105. The Heartware® VAD pump 105, which may be a new generation HVAD centrifugal flow VAD, is smaller device than the HeartMate® II VAD pump 105. In some embodiments, the larger HeartMate® II device requires a VAD controller 138 (shown in FIG. 3A) and a VAD battery 144 (shown in FIG. 3A and FIG. 3C) that is taller than the their equivalent components in a Heartware® VAD pump 105. In accordance, the water-resistant VAD lifestyle bag 100 utilized for the HeartMate® II Blood Pump or a Heartware® Blood Pump will differ in dimensions.

The VAD pump 105 may be implanted alongside a patient's 102 heart's left ventricle or may be placed just below the diaphragm in the abdomen. The VAD pump 105 may be attached to the aorta and leave natural circulation in place while providing all of the energy necessary to propel blood throughout the patient's 102 body. In certain embodiments, the VAD pump 105 may pump up to 10 liters of blood per minute covering the full output of a healthy heart, and provide long-term cardiac support for patients who have advanced-stage heart failure. In some embodiments, the VAD pump 105 is about 55 cubic centimeters and about 160 grams and includes an impeller that is suspended through a combination of passive magnetic and hydrodynamic forces.

Figure 2A:
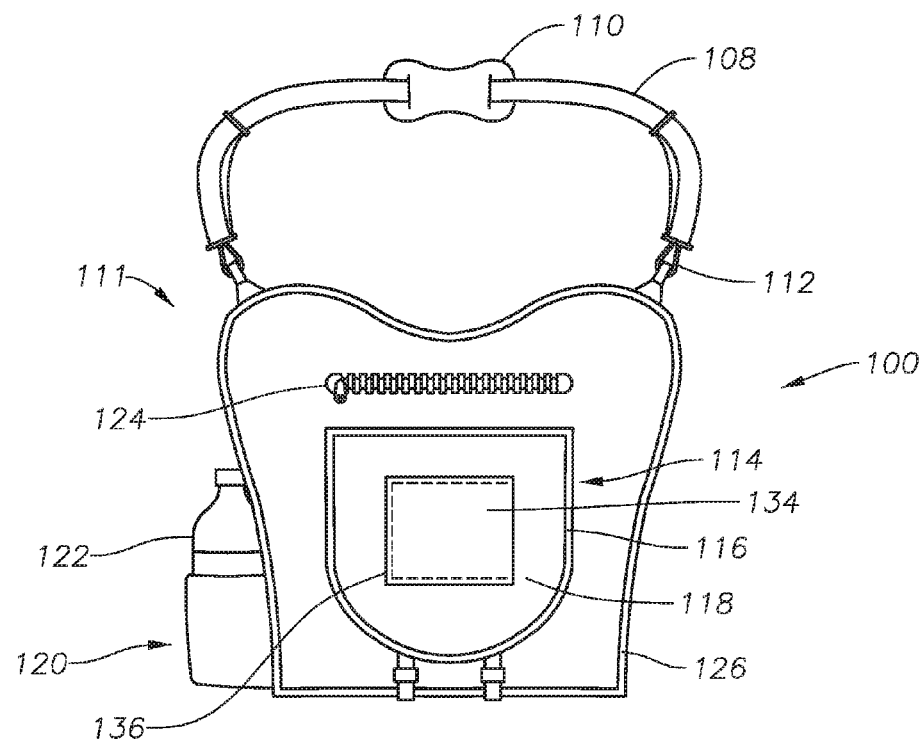
FIG. 2A is a front view of the water-resistant VAD lifestyle bag according to an embodiment.

Shown in FIG. 2A is a front view of the water-resistant VAD lifestyle bag 100 according to at least embodiment. The water-resistant VAD lifestyle bag 100 includes a removable strap 108 connected to two connectors 112 along the top of the bag 100, a lower unit 111 having two curved top edges connected to two connectors 112 and having at least one water bottle pocket 120 to contain water bottles 122 of various shapes and a front pocket cover flap 118, a zipper 124 configured along the top of the lower unit 111, an emergency information window 134 made of clear material to view the status of a VAD device 132, a plurality of pockets 158 built into the back of the bag 100 (shown in FIG. 4B), at least one credit card pocket 160 built into the bag 100 (shown in FIG. 4B), a controller pocket 140 having clips 141 and configured to secure a VAD controller 138 (shown in FIG. 3A and FIG. 3B), and at least one battery pocket 142 having clips 141 and fitted to house at least one VAD battery 144 for powering the VAD device 132 (shown in FIG. 3A and FIG. 3C). The VAD device 132 may be a HeartMate® VAD or a Heartware® VAD, which may be coupled to a VAD pump 105. The plurality of pockets 158 is located on the backside, which may be the side not having the front over pocket 114, of the water-resistant VAD lifestyle bag 100. In certain embodiments, the exterior of the water-resistant VAD lifestyle bag 100 is constructed of a double layer, water-resistant lining fabric with a foam inserted between the lining fabric layers to create firmness and maintain shape, wherein the foam is ⅛ inch polypropylene, dust-free, non-abrasive, shock resistant and moisture proof sewn with German Thread Strongbond 40-T70 V69 and Serabond 30-T90-V92 with up to 12 stiches per inch.

In certain embodiments, the water-resistant VAD lifestyle bag 100 is lined with a bag webbing 126, which may be 1 inch thick and may outlined and bind to the bag 100. In some embodiments, the water-resistant VAD lifestyle bag 100 is 12 inches long at the top of the bag, 13.5 inches high, 11 inches long at the bottom of the bag or is 14.25 inches long at the top of the bag, 11.5 inches high, and 11.5 inches long at the bottom of the bag, and with a 2 inches seam ending at the top of the bag. In certain embodiments, the water-resistant VAD lifestyle bag 100 includes a zipper 124 that is a #8 zipper chain of 10 inches long or a #10 zipper chain of 12 inches long, with water-resistant lining fabric. In certain embodiments, the emergency information window 134 is 6.5 inches by 6.5 inches, is constructed of 30,000 super clear plastic, and is surrounded by an emergency information window frame 136 that may be of a water-resistant lining material. In some embodiments, the at least one water bottle pocket 120 is constructed of 1,000 Denier Nylon Cordura Coated DWR $1^{st}$ Fabric and has a plastic inserted of 0.25 inch thick plastic.

Figure 2B:
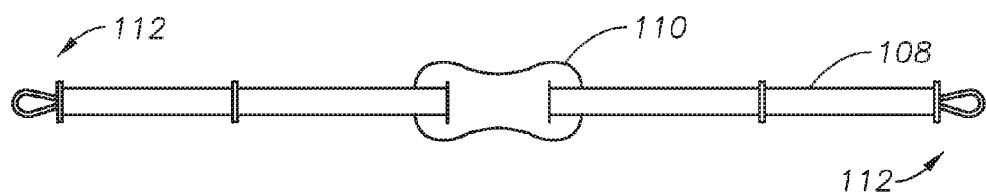
FIG. 2B is a view of the removable strap of the water-resistant VAD lifestyle bag according to an embodiment.

Shown in FIG. 2B is a view of the removable strap 108 of the water-resistant VAD lifestyle bag 100 according to an embodiment. A shoulder pad 110 may slide onto or be attached to the removable strap 108, and may be prevented from being removed from the removable strap 108 by the two connectors 112. In some embodiments, the removable strap is 56 inches in length.

Figure 2C:
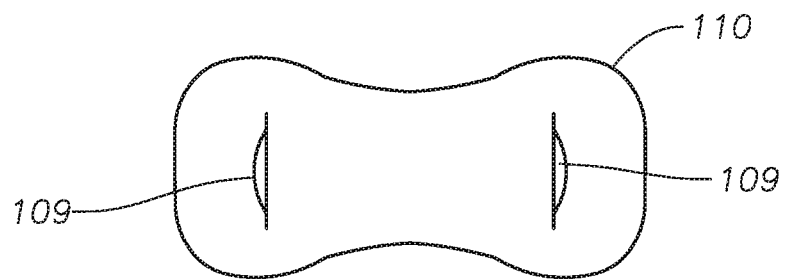
FIG. 2C is a close-up view of shoulder pad of the removable strap of the water-resistant VAD lifestyle bag according to an embodiment.

Shown in FIG. 2C is a close-up view of shoulder pad 110 of the removable strap 108, which may be about 1 inch wide, of the water-resistant VAD lifestyle bag according to an embodiment. The shoulder pad 100 contains holes 109 which enable the removable strap 108 to snugly be coupled to the shoulder pad. Thus, for example, the hole 109 may be about 1 inch wide, and allow an about 1 inch wide removable strap to fit inside. Each hole 109 is sized to enable the shoulder pad 110 to slide along the removable strap 108 but not oversized to cause unnecessary motion of the removable strap 108.

Figure 3A:
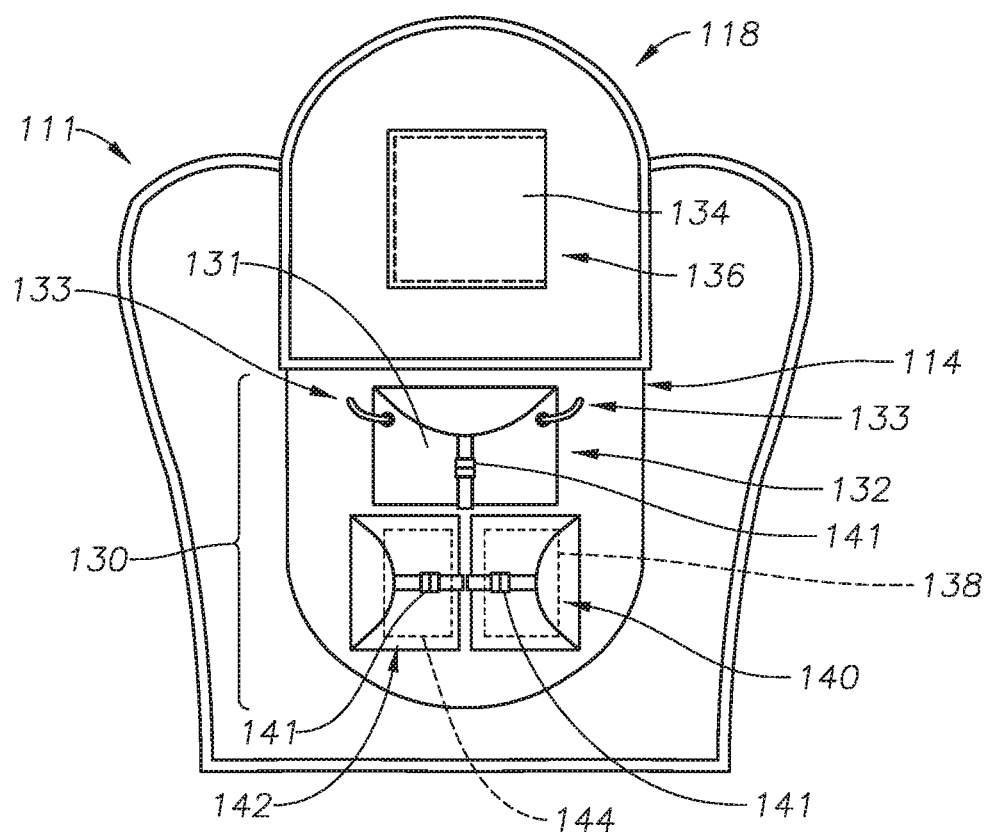
FIG. 3A is an internal view of the water-resistant VAD lifestyle bag with an open front cover pocket according to an embodiment.

Shown in FIG. 3A is an internal view of the water-resistant VAD lifestyle bag 100 with an open front cover pocket 114 according to an embodiment. The front cover pocket 114 may be opened by a patient 102 lifting the front pocket cover flap 118 away from the water-resistant lifestyle VAD bag 100. The emergency information window 134 allows a patient 102 to view indicators on at least one of the VAD device 132, VAD controller 138, and VAD battery 144. A patient may lift up the front cover pocket 114 to view more than the indicators, such as for example the full view or full operation, of each of the VAD device 132, VAD controller 138, and VAD battery 144.

In certain embodiments, at least one of the VAD device 132, VAD controller 138, and VAD battery 144 may be attached to the water-resistant VAD lifestyle bag 100 with a hook 133, which is mated with a hole on the pockets that enclose the VAD device 132, VAD controller 138, and VAD battery 144. Thus, for example, a VAD device pocket 131, which may enclose the VAD device 132, may be coupled to the water-resistant VAD lifestyle bag 100 with a hook 133. Thus, for example, the VAD controller pocket 140, which may enclose the VAD controller 138, may be coupled to the water-resistant VAD lifestyle bag 100 with a hook 133. Thus, for example, the VAD battery pocket 142, which may enclose at least one VAD battery 144, may be coupled to the water-resistant VAD lifestyle bag 100 with a hook 133. In certain embodiments, a clip 141 may keep closed each of the VAD device pocket 131, the VAD controller pocket 140, and the VAD battery pocket 142, and ensure that no water of moisture enter or penetrates inside the exemplary pockets.

In some embodiments, the VAD controller pocket 140 and the at least one VAD battery pocket 142 is outlined with polypropylene piping with a ⅛ inch polypropylene cord, lined with waterproof lining of 200 Denier Oxford Coated DWR fabric, and contains a styrene insert to maintain the firm shape of the bag. The emergency information window 134 is constructed of 30,000 super clear plastic and with a zipper chain of 8 inches length.

In certain embodiments, by attaching the VAD device pocket 131, the VAD controller pocket 140, and the VAD battery pocket 142 with the lower unit and connecting the removable strap 108 to the connectors 112, the water-resistant VAD lifestyle bag 100 is assembled. Thus, for example, the water-resistant VAD lifestyle bag 100, which stores a VAD device 132 sensitive to water damage, can be assembled by providing a removable strap 108 connected to two connectors 112 along the top of the bag 100 and having a shoulder pad 110, providing a lower unit 111 having two curved top edges connected to two connectors 112 and having at least one water bottle pocket 120 to contain water bottles 122 of various shapes and a front pocket cover flap 118, closing the VAD controller pocket 140 with the clips 141, and closing the VAD battery pocket 142 with the clips 141. In some embodiments, during the exemplary method of making a water-resistant VAD lifestyle bag 100 for storing a VAD device 132 sensitive to water damage, the lower unit 111 may include a zipper 124 configured along the top of the lower unit 111, an emergency information window 134 made of clear material to view the status of a VAD device 132, a plurality of pockets 158 built into the back of the bag 100, at least one credit card pocket 160 built into the bag 100, a VAD controller pocket 140 having clips 141 and configured to secure a VAD controller 138, and at least one VAD battery pocket 142 having clips 141 and fitted to house at least one VAD battery 144 for powering the VAD device 132. Thus, for example, the water-resistant VAD lifestyle bag 100 provides for multiple and redundant mechanisms to prevent water and moisture from contacting each of the VAD device 132, the VAD controller 138, and the at least one VAD battery 144.

Figure 3B:
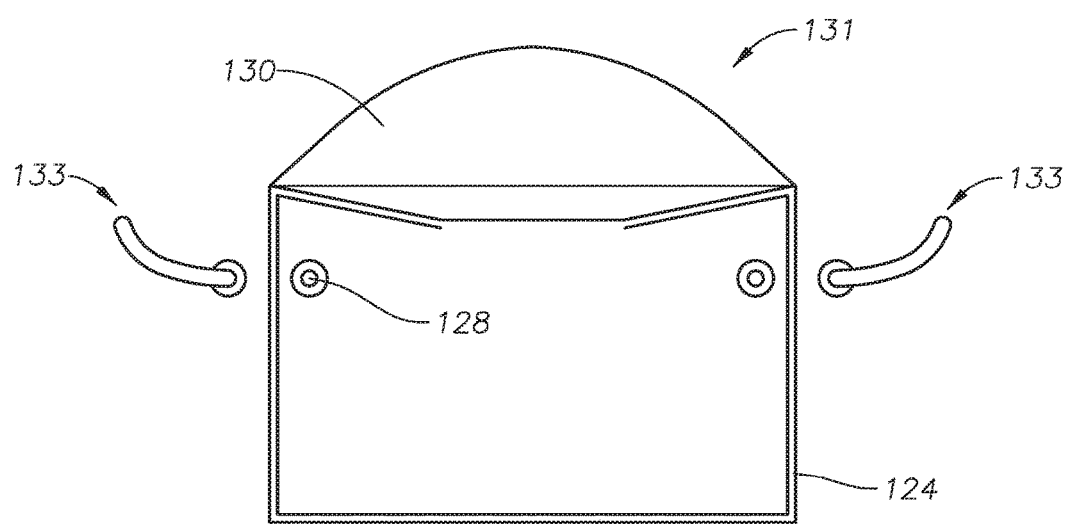
FIG. 3B is a view of the VAD device pocket of the water-resistant VAD lifestyle bag according to an embodiment.

Shown in FIG. 3B a view of the VAD device pocket 131 of the water-resistant VAD lifestyle bag 100 according to an embodiment. The VAD device pocket 131 is configured to block entry of moisture to the VAD device 132. The VAD device pocket 131 may include a VAD device flap 130 and hook holes 129. The hooks 133 attached to the lower unit 111 may pass through the hook holes 129 to hold the VAD device pocket 131 secure with the lower unit 111. In certain embodiments, the VAD device pocket 131 may be lined with a piping 129 that may be 5 inches by 5.5 inches by 0.25 inches. The piping 129 provides redundancy against water and moisture exposure to the VAD device 132 and provides firmness to the shape of the VAD device pocket 131. In a method of assembling the water-resistant VAD lifestyle bag 100, the hooks 133 are positioned through the hook holes 129 and the VAD device flap 130 is sealed closed against the hooks 133 to provide redundant closure of the VAD device inside of the VAD device pocket 131.

Figure 3C:
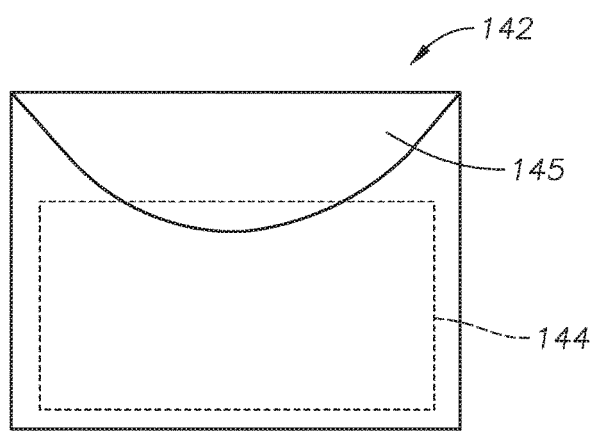
FIG. 3C is a view of the VAD battery pocket of the water-resistant VAD lifestyle bag according to an embodiment.

Shown in FIG. 3C is a view of the VAD battery pocket 142 of the water-resistant VAD lifestyle bag 100 according to an embodiment. The VAD battery pocket 142 is configured to block entry of moisture to the at least one VAD battery 144. The VAD battery pocket 142 is 4.25 inches by 3.25 inches by 1.75 inches, and may include a VAD batter pocket flap 145 that closes shut to seal the at least one VAD battery inside of the VAD battery pocket 142.

Figure 4A:
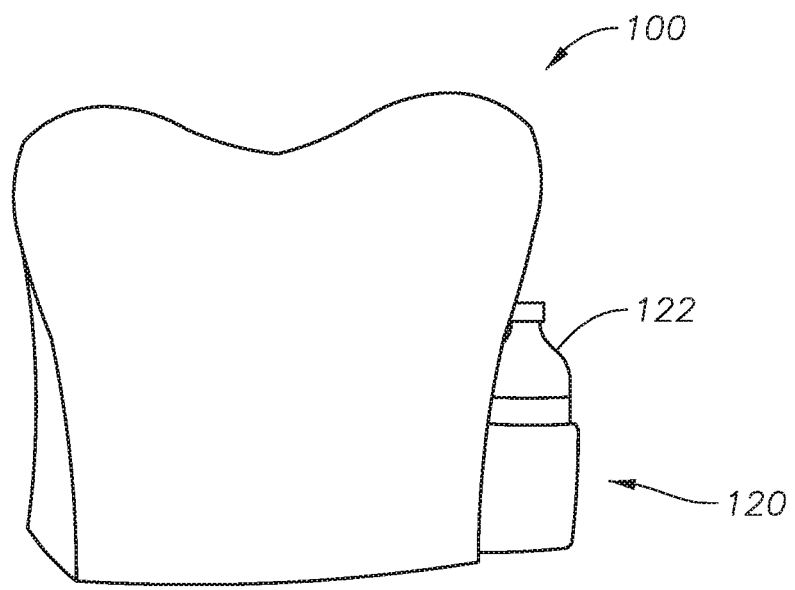
FIG. 4A is a back view of the water-resistant VAD lifestyle bag according to an embodiment.

Shown in FIG. 4A is a back view of the water-resistant VAD lifestyle bag according to an embodiment. In some embodiments, the at least one water bottle pocket 120 comprises a bottom hole of ⅝ inch and is 6 inches tall by 7 inches around and may hold a water bottle 122. In certain embodiments, the water bottle pocket 120 may be pouch for holding soda cans, coffee cups, or milk cartons.

Figure 4B:
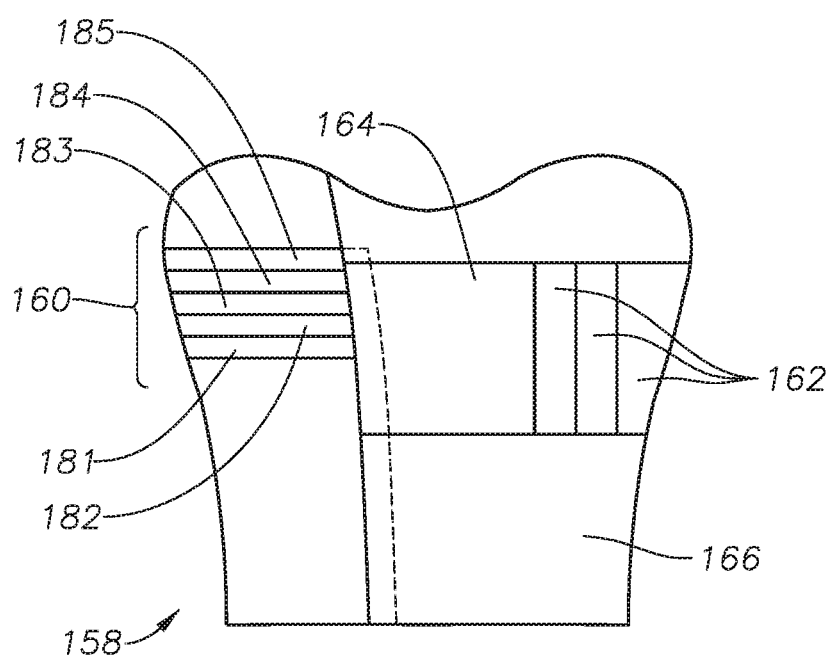
FIG. 4B is a back view of the water-resistant VAD lifestyle bag with a plurality of pockets built into the back of the bag according to an embodiment.

Shown in FIG. 4B is a back view of the water-resistant VAD lifestyle bag 100 with a plurality of pockets 158 built into the back of the bag 100 according to an embodiment. In some embodiments, the plurality of pockets 158 is configured to secure at least one of pens, phones, and snacks. The plurality of pockets 158 is constructed of 1,000 Denier Oxford Coated DWR 1$^{st}$ fabric and optionally sewn over with water-resistant lining fabric. The at least one credit card pocket 158 further comprises a first credit card pocket 181 that is 5 inches by 2.25 inches, a second credit card pocket 182 that is 4.75 inches by 2.25 inches, a third credit card pocket 183 that is 4.25 inches by 2.25 inches, a fourth credit card pocket 184 that is 4⅜ inches by 2.25 inches, and a fifth credit card pocket 185 that is 4.25 inches by 2.25 inches. The plurality of pockets 158 may further comprise at least one of a pen pocket 162 that is 0.25 inch by 6 inches, a phone pocket 162 that is 5.25 inches by 7.25 inches, and a snack pocket 166 that is 7 inches by 4 inches. In certain embodiments, the plurality of pockets 158, which may include one or more of the at least one credit card pocket 158, the pen pocket 162, the phone pocket 162, and the snack pocket, can be constructed as a sleeve that is partially open to allow the patient 102 to easily insert and remove lifestyle accessories.

Figure 4C:
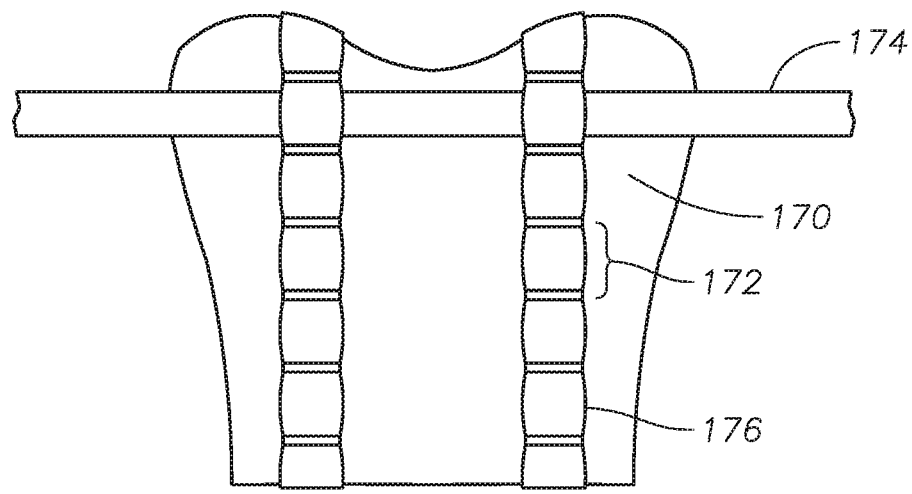
FIG. 4C is a back view of the water-resistant VAD lifestyle bag with at least one belt loop sewn onto the back of the bag according to an embodiment.

Shown in FIG. 4C is a back view of the water-resistant VAD lifestyle bag 100 with at least one belt loop 172 sewn onto the back of the bag 100 according to an embodiment. The at least one belt loop 172 sewn onto the back of the bag 100 and may hold onto a belt 174. The at least one belt loop 172 may have seams 2.25 inches apart and made of P 2,200 with 2,000 webbing with UV inhibitors.

Figure 4D:
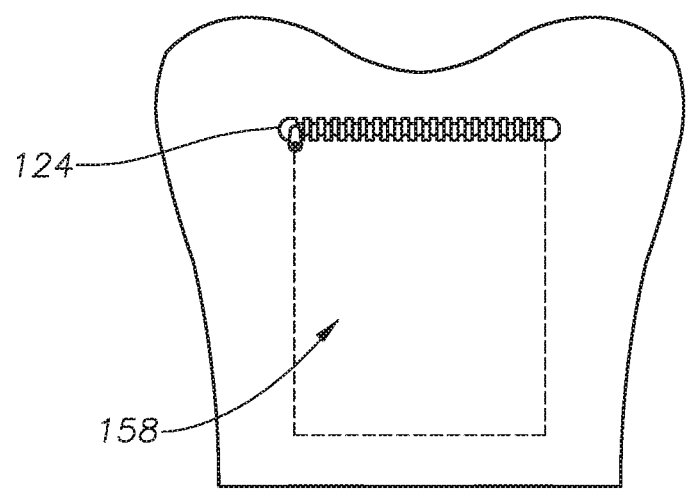
FIG. 4D is a back view of the water-resistant VAD lifestyle bag with a sewn extra pocket onto the back of the bag according to an embodiment.

Shown in FIG. 4D is a back view of the water-resistant VAD lifestyle bag 100 with a sewn extra pocket 168 onto the back of the bag 100 according to a dimensioned embodiment. The sewn extra pocket 168 may be 4.75 inches by 2.25 inches and may be coupled with a zipper 124 onto the back of the bag 100.

In certain embodiments, the water-resistant lifestyle VAD bag 100 as shown in FIGS. 1, 2A, 2B, 3A, 4A, 4B, 4C, and 4D may include internal walls, exterior walls, internal sleeves, an inner layer, and pockets that may be constructed with 1050 Denier Nylon Ballistic cloth coated condura fabric, which provides water-resistant properties. In certain embodiments, the construction of and the components of the water-resistant lifestyle VAD bag 100 may consist of styrene 0.030, polypropylene black piping, waterproof lining, P2200 webbing with UV inhibitors, and foam ⅛" polyethylene. In some embodiments, the construction of and the components of the water-resistant lifestyle VAD bag 100 may be dust-free, non-abrasive, shock resistant, and moisture proof.

One of ordinary skill in the relevant art would have understood that the components of the water-resistant lifestyle VAD bag 100 described above may be constructed of other materials that may provide the bag or pouch with similar characteristics (i.e., dust free, non-abrasive, shock resistant, moisture proof, water proof, etc.).

Although the technology herein has been described with reference to particular embodiments, it is to be understood that these embodiments are merely illustrative of the principles and applications. It is therefore to be understood that numerous modifications can be made to the illustrative embodiments and that other arrangements can be devised without departing from the spirit and scope as defined by the appended claims.

What is claimed is:

1. A water-resistant ventricular assist device (VAD) lifestyle bag, comprising:
   a removable strap connected to two connectors along the top of the VAD lifestyle bag and comprising a shoulder pad;
   a lower unit having two curved top edges connected to two connectors and comprising at least one water bottle pocket to contain water bottles of various shapes and a front pocket cover flap;
   a zipper configured along the top of the lower unit;
   an emergency information window made of clear material to view the status of a VAD device;
   a plurality of pockets built into the back of the VAD lifestyle bag configured to secure at least one of pens, phones, and snacks;
   at least one credit card pocket built into the VAD lifestyle bag;
   a VAD controller pocket comprising clips and configured to secure a VAD controller; and
   at least one VAD battery pocket comprising clips and fitted to house at least one VAD battery for powering the VAD device,
   wherein the VAD controller pocket and the at least one VAD battery pocket is outlined with polypropylene piping with a ⅛ inch polypropylene cord, lined with waterproof lining of 200 Denier Oxford Coated DWR fabric, and contains a styrene insert to maintain the firm shape of the VAD lifestyle bag.

2. The water-resistant VAD lifestyle bag of claim 1, wherein the VAD controller pocket is configured to block entry of moisture to the VAD controller.

3. The water-resistant VAD lifestyle bag of claim 1, wherein the VAD battery pocket is configured to block entry of moisture to the at least one VAD battery.

4. The water-resistant VAD lifestyle bag of claim 1, wherein the at least one water bottle pocket is constructed of 1,000 Denier Nylon Cordura Coated DWR 1$^{st}$ Fabric and having a plastic inserted of 0.25 inch thick plastic.

5. The water-resistant VAD lifestyle bag of claim 1, wherein the emergency information window is constructed of 30,000 super clear plastic and with a zipper chain of 8 inches length.

6. The water-resistant VAD lifestyle bag of claim 1, wherein the plurality of pockets is constructed of 1,000 Denier Oxford Coated DWR 1$^{st}$ fabric and sewn over with water-resistant lining fabric.

7. The water-resistant VAD lifestyle bag claim 1, wherein the VAD lifestyle bag is 12 inches long at the top of the VAD lifestyle bag, 13.5 inches high, 11 inches long at the bottom of the VAD lifestyle bag or is 14.25 inches long at the top of the VAD lifestyle bag, 11.5 inches high, and 11.5 inches long at the bottom of the VAD lifestyle bag, and with a 2 inches seam ending at the top of the VAD lifestyle bag.

8. The water-resistant VAD lifestyle bag of claim 1, further comprising:
   at least one belt loop sewn onto the back of the VAD lifestyle bag for holding onto a belt and with seams 2.25 inches apart and made of P 2,200 with 2,000 webbing with UV inhibitors or a sewn extra pocket 4.75 inches by 2.25 inches coupled with a zipper onto the back of the VAD lifestyle bag.

9. The water-resistant VAD lifestyle bag of claim 1, wherein the emergency information window is 6.5 inches by 6.5 inches.

10. The water-resistant VAD lifestyle bag of claim 1, wherein the VAD battery pocket is 4.25 inches by 3.25 inches by 1.75 inches.

11. The water-resistant VAD lifestyle bag of claim 1, wherein the plurality of pockets further comprise at least one of a pen pocket 0.25 inch by 6 inches, a phone pocket of 5.25 inches by 7.25 inches, and a snack pocket 7 inches by 4 inches.

12. The water-resistant VAD lifestyle bag of claim 1, wherein at least one credit card pocket further comprises a first credit card pocket 5 inches by 2.25 inches, a second credit card pocket 4.75 inches by 2.25 inches, a third credit card pocket 4.25 inches by 2.25 inches, a fourth credit card pocket 4⅜ inches by 2.25 inches, and a fifth credit card pocket 4.25 inches by 2.25 inches.

13. The water-resistant VAD lifestyle bag of claim 1, wherein the removable strap is 56 inches in length.

14. The water-resistant VAD lifestyle bag of claim 1, wherein the zipper is a #8 zipper chain of 10 inches long or a #10 zipper chain of 12 inches long.

15. The water-resistant VAD lifestyle bag of claim 1, wherein the bag exterior of the bag is constructed of a double layer, water-resistant lining fabric and wherein the styrene insert is ⅛ inch polypropylene, dust-free, non-abrasive, shock resistant and moisture proof sewn with German Thread Strongbond 40-T70 V69 and Serabond 30-T90-V92 with up to 12 stiches per inch.

16. A water-resistant VAD lifestyle system, comprising:
   a water-resistant VAD lifestyle bag, comprising:
      a removable strap connected to two connectors along the top of the bag and comprising a shoulder pad;
      a lower unit having two curved top edges connected to two connectors and comprising at least one water bottle pocket to contain water bottles of various shapes and a front pocket cover flap;
      a zipper configured along the top of the lower unit;
      an emergency information window made of clear material to view the status of a VAD device;
      a plurality of pockets built into the back of the bag configured to secure at least one of pens, phones, and snacks;
      at least one credit card pocket built into the bag;
      a VAD controller pocket comprising clips and configured to secure a VAD controller; and
      at least one VAD battery pocket having clips and fitted to house at least one VAD battery for powering the VAD device; and
   a water-resistant percutaneous lead for electrically coupling the VAD controller to a VAD pump and for regulating VAD pump function
   wherein the VAD controller pocket and the at least one VAD battery pocket is outlined with polypropylene pipping with a ⅛ inch polypropylene cord, lined with waterproof lining of 200 Denier Oxford Coated DWR fabric, and contains a styrene insert to maintain the firm shape of the VAD lifestyle bag.

17. A method of making a water-resistant VAD lifestyle bag for storing a VAD device sensitive to water damage, the method comprising:

provideing a removable strap connected to two connectors along the top of the bag and comprising a shoulder pad;

providing a lower unit having two curved top edges connected to two connectors and comprising at least one water bottle pocket to contain water bottles of various shapes and a front pocket cover flap, the lower unit comprising;

a zipper configured along the top of the lower unit;

an emergency information window made of clear material to view the status of a VAD device;

a plurality of pockets built into the back of the bag configured to secure at least one of pens, phones, and snacks;

at least one credit card pocket built into the bag;

a VAD controller pocket comprising clips and configured to secure a VAD controller; and at least one VAD battery pocket having clips and fitted to house at least one VAD battery for powering the VAD device; and closing the VAD controller pocket with the clips; and closing the VAD battery pocket with the clips, wherein the VAD controller pocket and the at least one VAD battery pocket is outlined with polypropylene pipping with a ⅛ inch polypropylene cord, lined with waterproof lining of 200 Denier Oxford Coated DWR fabric, and contains a styrene insert to maintain the firm shape of the VAD lifestyle bag.

* * * * *